(12) United States Patent
Niederberger

(10) Patent No.: US 7,946,189 B2
(45) Date of Patent: May 24, 2011

(54) LIQUID SAMPLE STATION

(76) Inventor: Johann Niederberger, Aurora, IL (US)

( * ) Notice: Subject to any disclaimer, the term of this patent is extended or adjusted under 35 U.S.C. 154(b) by 408 days.

(21) Appl. No.: 11/992,686

(22) PCT Filed: Sep. 25, 2006

(86) PCT No.: PCT/US2006/037044
§ 371 (c)(1),
(2), (4) Date: Mar. 26, 2008

(87) PCT Pub. No.: WO2007/041036
PCT Pub. Date: Apr. 12, 2007

(65) Prior Publication Data
US 2010/0162833 A1    Jul. 1, 2010

Related U.S. Application Data

(60) Provisional application No. 60/721,828, filed on Sep. 29, 2005.

(51) Int. Cl.
*G01N 1/00*     (2006.01)
(52) U.S. Cl. .......................................... 73/863

(58) Field of Classification Search ................... 73/863, 73/863.71–863.73, 864
See application file for complete search history.

(56) References Cited

U.S. PATENT DOCUMENTS

| | | | | | |
|---|---|---|---|---|---|
| 2,245,679 | A | * | 6/1941 | Kelley | 73/863.02 |
| 5,115,686 | A | * | 5/1992 | Walker et al. | 73/863.31 |
| 5,116,330 | A | * | 5/1992 | Spencer | 73/863.71 |
| 5,131,282 | A | * | 7/1992 | Kuhner | 73/863.71 |
| 5,370,146 | A | * | 12/1994 | King et al. | 137/8 |

* cited by examiner

*Primary Examiner* — Hezron Williams
*Assistant Examiner* — Tamiko D Bellamy
(74) *Attorney, Agent, or Firm* — Sandra Thompson; John C. Thompson

(57) ABSTRACT

A sample station and method of using the station, which contains a removable receptacle for collecting fluid samples from tanks, pipelines or other receptacles. The removable receptacle has a valve at the bottom for easy emptying and cleaning. The sample station is vented so the sample receptacle can not be pressurized, and is meant to be piped to the container which holds the fluid to be sampled, so the sample can be collected without risk of splashing, and without risk of spilling.

18 Claims, 8 Drawing Sheets

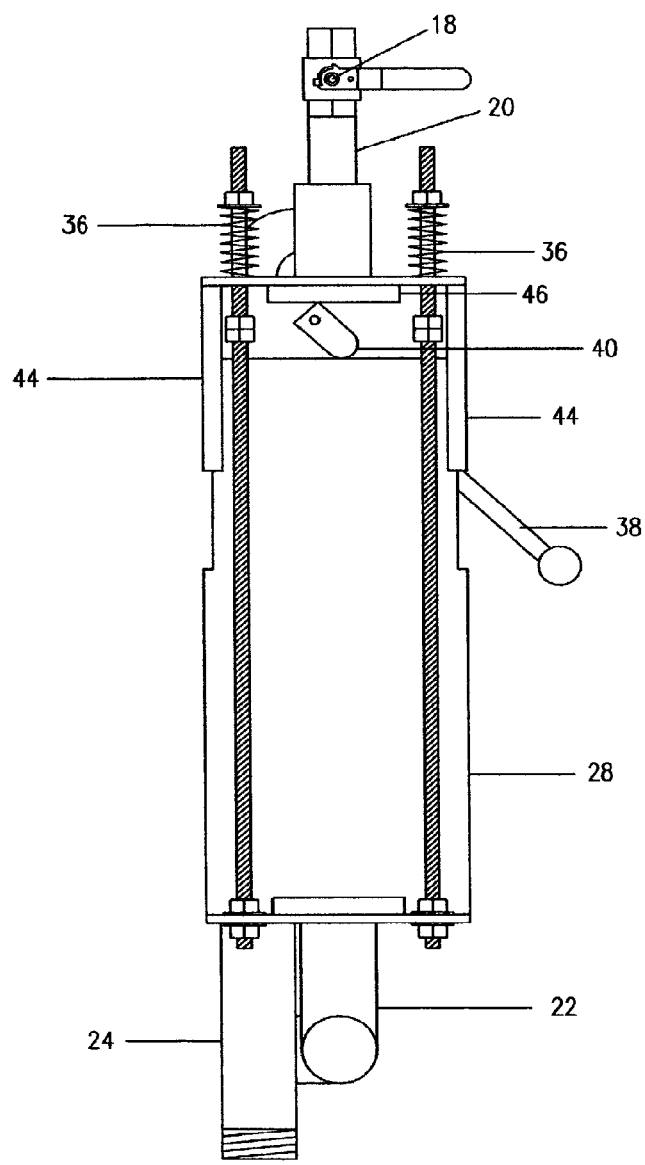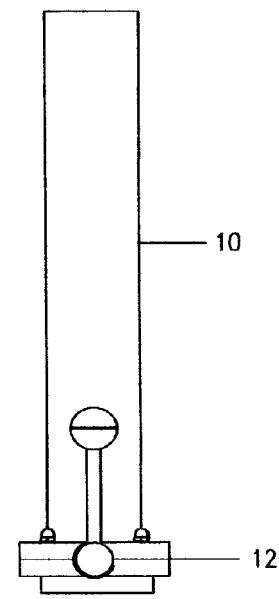
FIGURE 3
FIGURE 4

LIQUID SAMPLE STATION

CROSS-REFERENCE TO RELATED APPLICATIONS

This application claims benefit of Provisional Application Ser. No. 60/721,828, filed Sep. 29, 2005, hereby incorporated by reference.

TECHNICAL FIELD

The present invention relates to a method and apparatus for sampling fluid, more specifically a method and sampling apparatus which may be used to take a sample from hot or pressurized vessels or vessels which contain otherwise hazardous materials.

BACKGROUND OF THE INVENTION

It is well known in the art to take a sample from a discharge or other pipeline or from a storage, reaction, or other vessel, and discharge said sample into a sample container, such as a graduated cylinder, beaker or other measured container. However, when working with hazardous fluids, such as those with a high or low pH or high temperature or pressure, the sampling process may pose a hazard to the operator obtaining the sample. Operators frequently must don safety equipment to collect a sample, and may get some of the fluid to be sampled on exposed skin in spite of this. Sometimes liquid will splash out, or the sample container gets overfilled, causing excess liquid to run out of the sample holder and possibly onto the operator. Oftentimes, excess liquid will spill onto the surrounding area, causing a slip hazard or, in multi-level manufacturing facilities, especially chemical manufacturing facilities, which may be floored with only grating, endangering those working below. This invention should eliminate many of those hazards by piping the container to be sampled directly to the sample station, having an enclosed and vented receptacle for collecting the sample, and allowing the sample station discharge to be piped directly to a drain or a sump, from which it can be pumped back into the original container.

In many applications, it is desirable to visually inspect the fluid prior to sampling, for example to ensure that the fluid to be sampled is well-mixed, and many of the samplers currently known in the art do not have this capability. Additionally, some fluids may separate or are otherwise not always ready to be sampled. The liquid sample station with its transparent or translucent sample receptacle and flow through design overcomes both these problems.

OBJECTS AND SUMMARY OF THE INVENTION

It is an object of the present invention to provide a safe method of and apparatus for sampling fluids before, during, and after the manufacturing process. More particularly, it is an object of the present invention to provide a way for operators to safely collect a sample from a tank, pipeline or other receptacle which needs to be sampled, in a sample receptacle which is removable from the sample station for ease of transporting to a lab or other location where analysis of the sample will be done. Since the sample is piped directly into a vented receptacle, there will be no splash-back or spilling. Additionally, if the sample station is used for sampling a slurry or a liquid with sludge or other solids, the sample station can be used to check the concentration or volume of solids in the liquid in situ, then the sample receptacle can be emptied through the bottom valve into a drain line without removing the sample receptacle. If a sample of a liquid that separates or otherwise may not be ready to sample immediately upon opening the valve to the sampler is desired, the liquid can be run through the sampler until such time as it is desirable to collect a sample.

A wash water line installed upstream of the sample station allows the sample receptacle to be easily rinsed in place, without needing to remove it to wash it.

BRIEF DESCRIPTION OF THE FIGURES

FIG. 3 is a front view of the second embodiment of the sample station with the sample receptacle removed.

FIG. 4 shows the sample receptacle.

DETAILED DESCRIPTION

Figure 1:
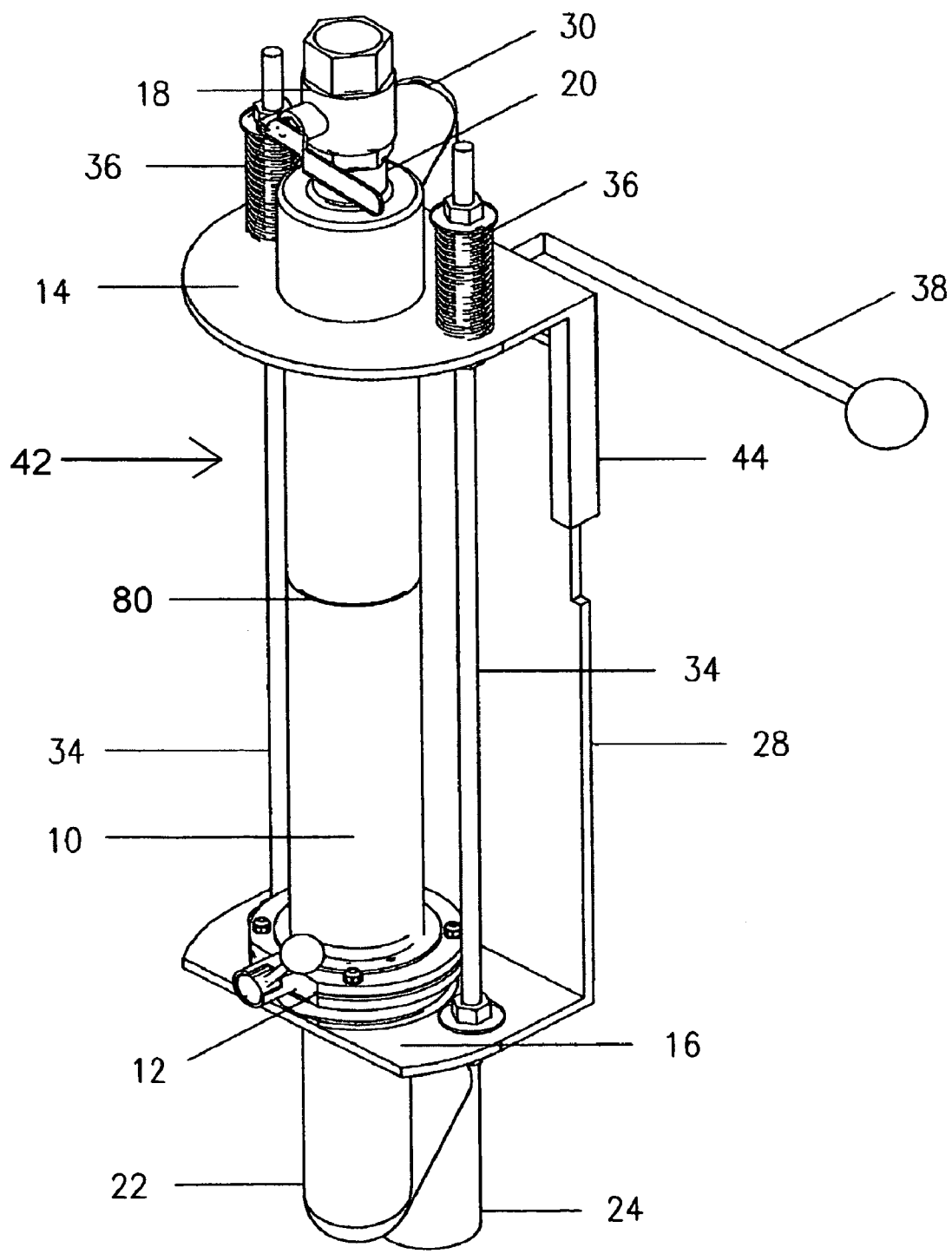
FIG. 1 illustrates a first embodiment of a sample station of this invention; which sample station includes a removable sample receptacle.

With reference initially to FIG. 1, a liquid sample station is shown generally at 8, the sample station including a sample receptacle 10 provided with an attached valve 12 at its lower end. The receptacle is mounted between first and second opposed upper and lower plates 14, 16, respectively, in a frame assembly generally shown at 42 in FIG. 3. A filling pipe 20, upstream of the sample receptacle has its downstream end attached to a collar of cylindrical flange 21 on the first opposing plate 14, allowing fluid to flow through the filling pipe and into the sample receptacle. The filling pipe has a filling valve 18, to control the flow of fluid into the sample receptacle. The second opposing plate has an opening with a drain line 22 attached to its circumference, allowing fluids to flow through the sample receptacle when the valve attached to the receptacle is open, or allowing the drainage of the sample receptacle if desired. The sample receptacle may be drained if it does not need to be removed for analysis, such as, for example, when a visual inspection is all that is needed. The drain line 22 ties into a drain/overflow pipe 24 as can best be seen from FIG. 5, which can drain to a floor drain or sump 52, (FIG. 8), or to a collection container 54, to allow the return of the fluid to its original vessel, as shown in FIG. 9.

The opposing plates are held roughly parallel to one another by attached support plates, a first support plate 26 (FIG. 7) holds the first opposing plate 14 and a second support plate 28 holds the second opposing plate 16. Channel shaped portions 44 on the sides of the first support plate partially wrap around the other support plate, serving to hold the two support plates in the proper orientation with respect to one another while allowing the plates to slide back and forth against each other. As shown, the first support plate 26 has the channel shaped portions 44, but the portions 44 could be on the second support plate as well.

Figure 2:
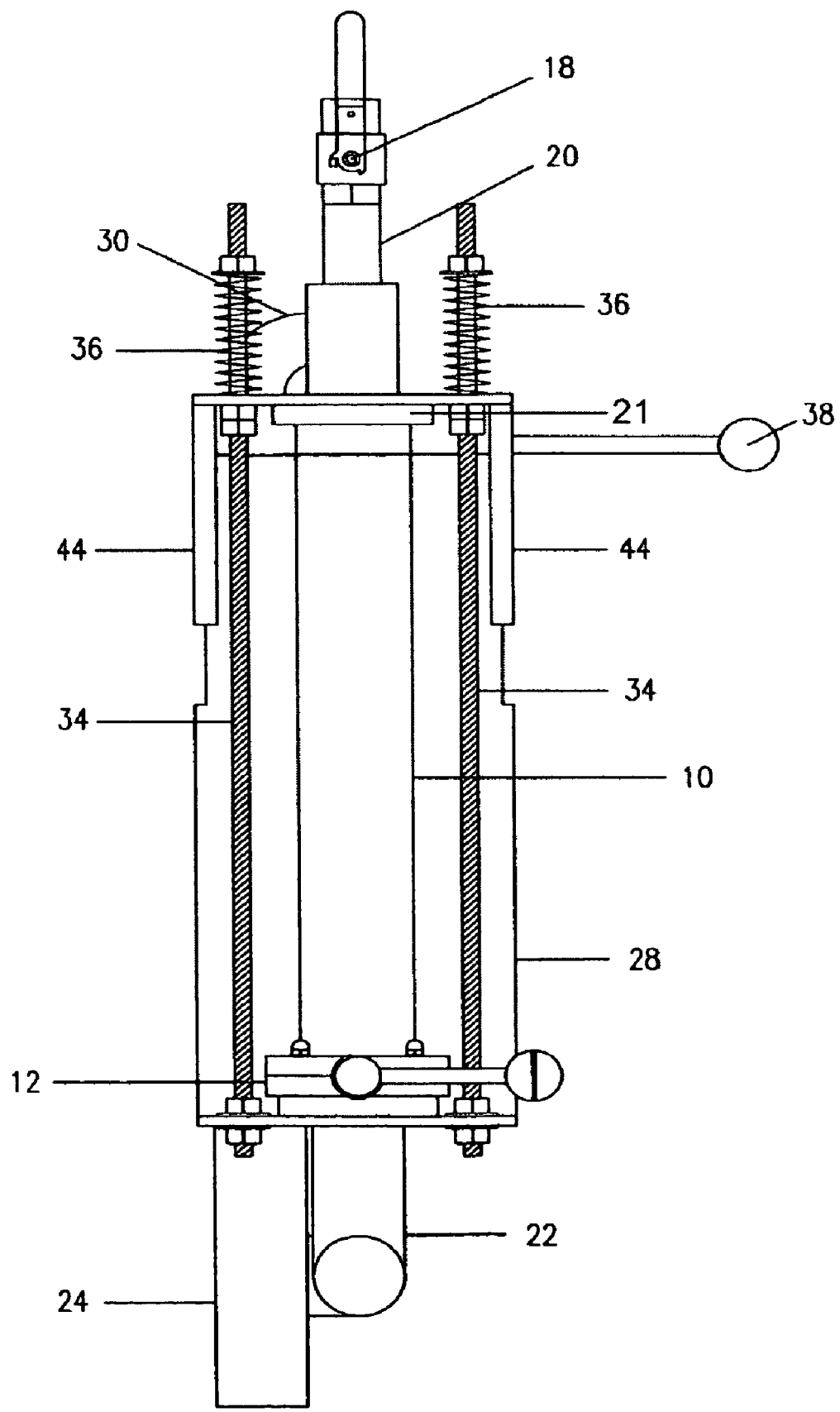
FIG. 2 is a front view of a second embodiment of a sample station with the sample receptacle.
Figure 5:
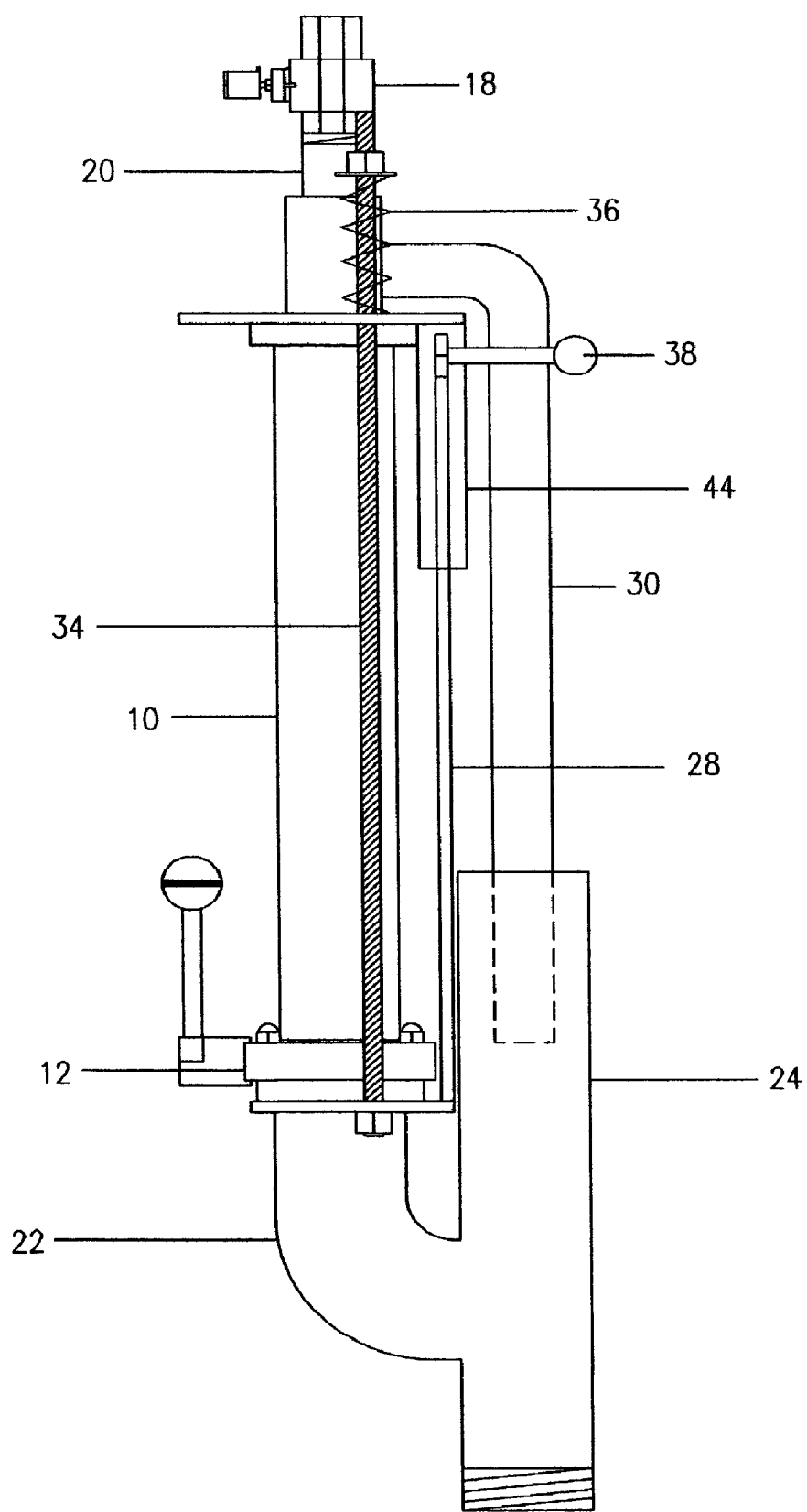
FIG. 5 is a side view of the first embodiment of the sample station with the sample receptacle.
Figure 6:
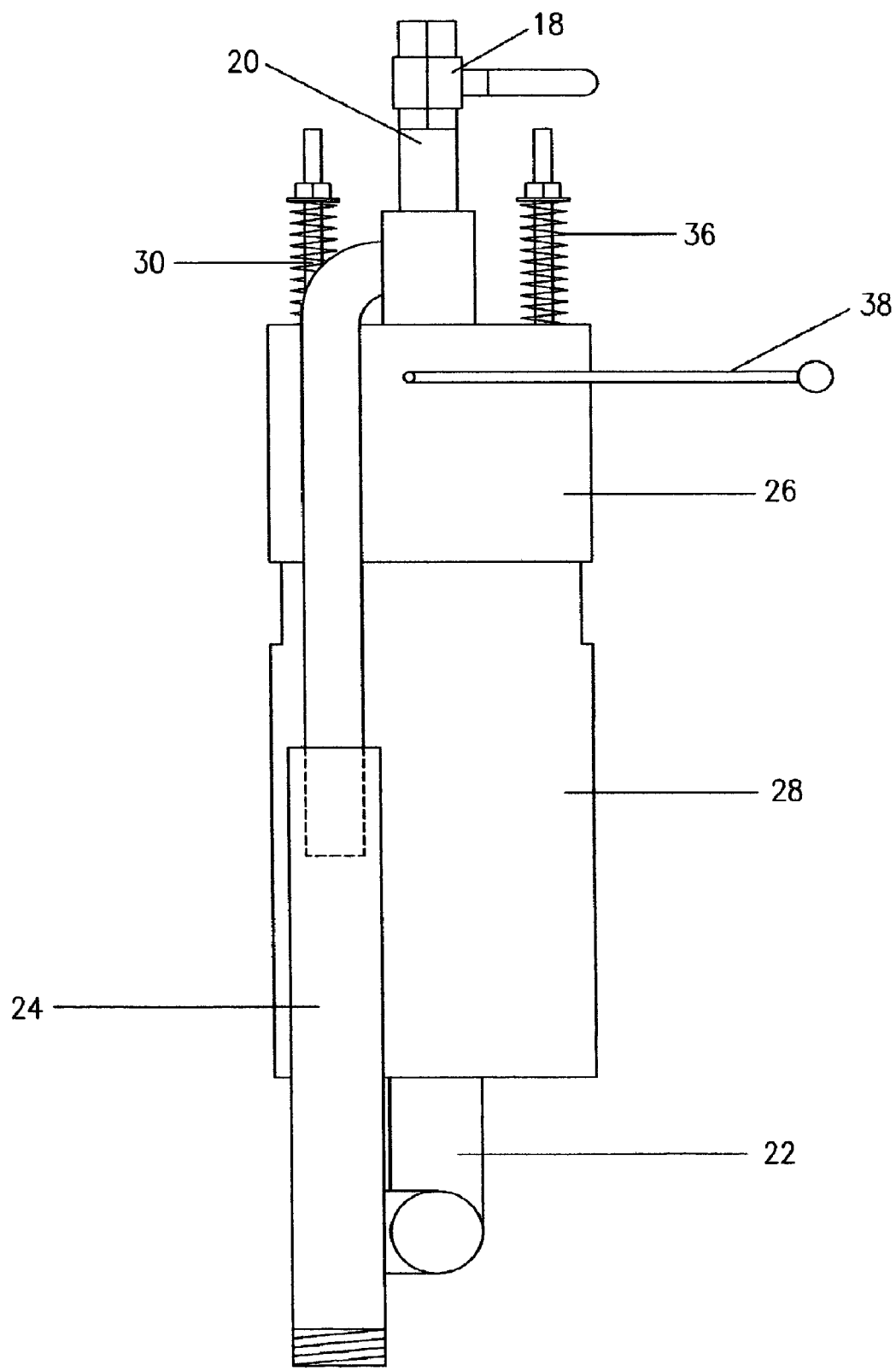
FIG. 6 is a back view of the second embodiment of the sample station.
Figure 7:
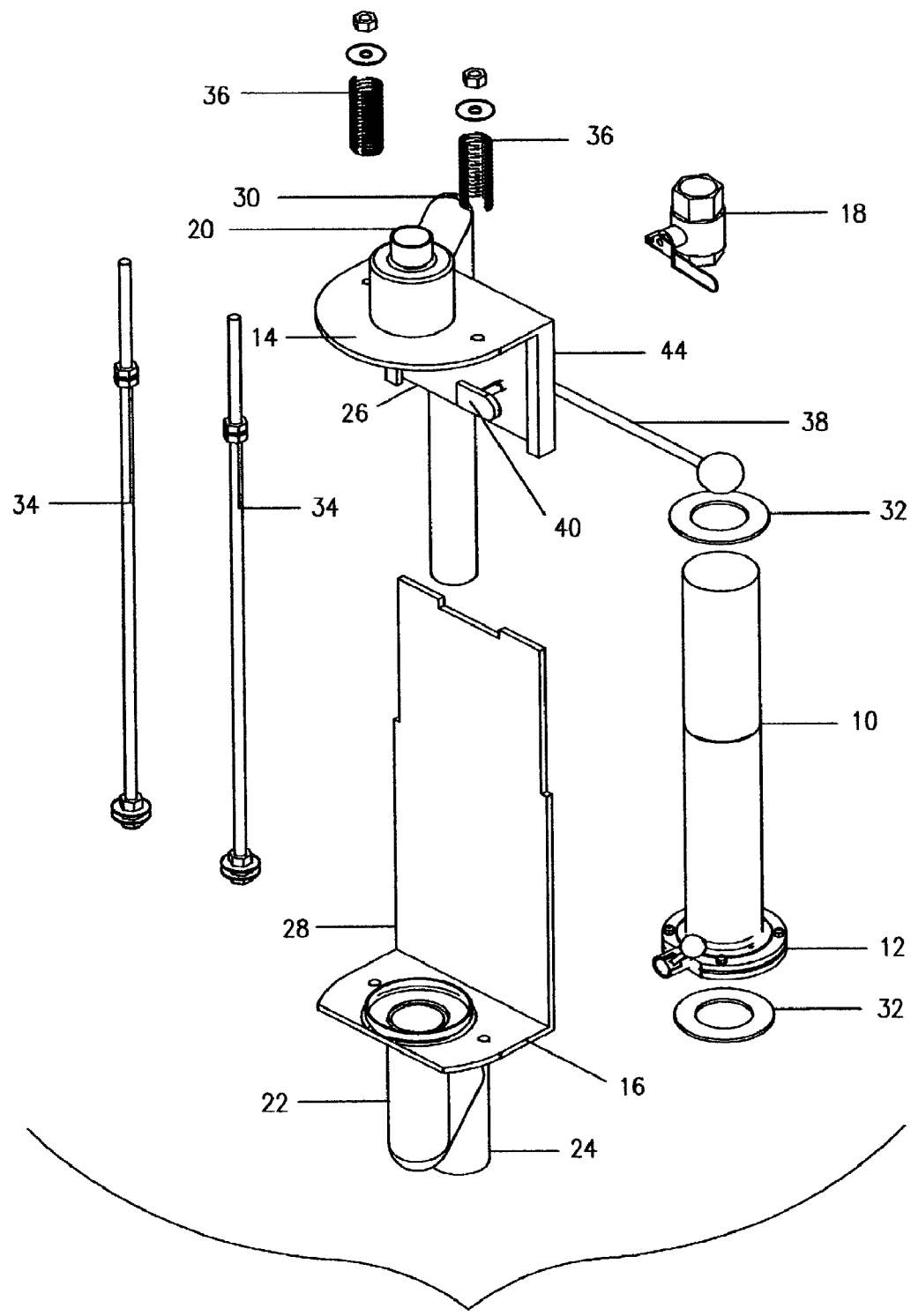
FIG. 7 is an exploded view of the first embodiment of the sample receptacle.

In the first embodiment illustrated in FIGS. 1, 5, and 7, an overflow/vent pipe 30 extends from the cylindrical flange 21 downwardly to the drain pipe 24, as best shown in FIG. 5. In the second embodiment illustrated in FIGS. 2, 3, and 6 the overflow/vent pipe extends from the filling pipe 20 to the drain pipe 24. In both embodiments this overflow/vent line allows filling the sample receptacle while preventing pressure from building up in the sample receptacle, and releases flashing vapors. It also allows for the accidental or deliberate overfilling of the sample receptacle without the risk of spilling, as any excess liquid would flow out through the overflow/vent line.

Figure 8:
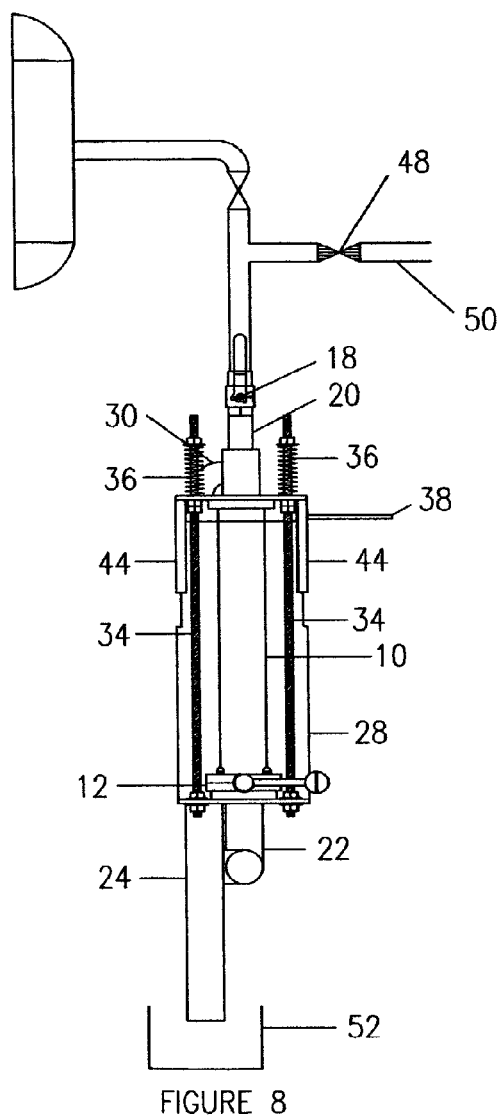
FIG. 8 is a front view of the second embodiment of the sample station with wash water piping and piping connecting it to a receptacle and a drain.
Figure 9:
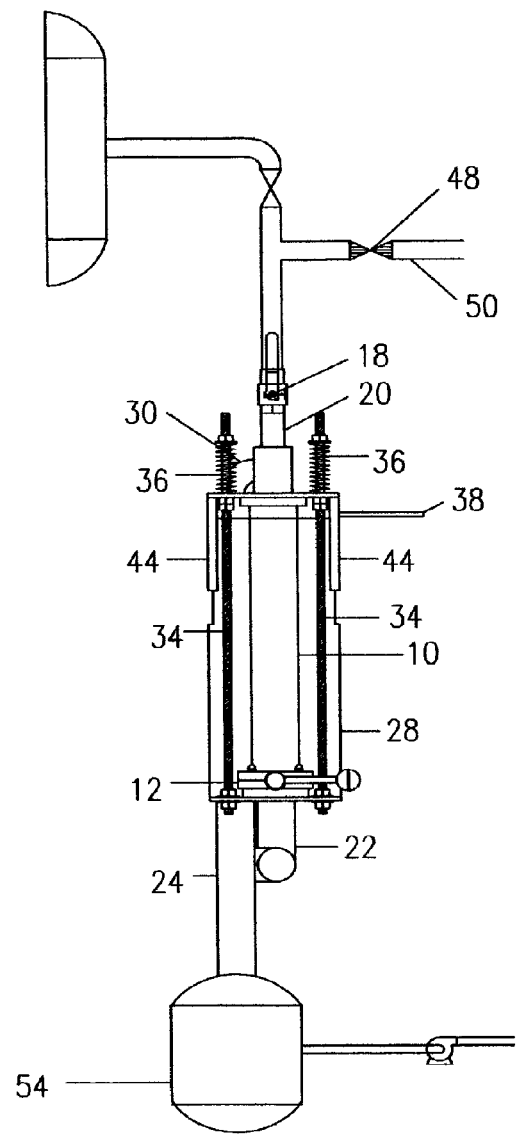
FIG. 9 is a front view of the second embodiment of the sample station with wash water piping and piping connecting it to a receptacle and a collection container

A wash water line 50 and wash water valve 48 can be installed upstream of the sample station, allowing the sample receptacle to be easily rinsed in place, without needing to remove it to wash it, as shown in FIG. 8 and FIG. 9.

Two gaskets 32, are accepted into depressions in the first and second opposing plates 14, 16. When the sample receptacle and its associated valve are sandwiched between the plates, the gaskets 32 help form a fluid-proof seal between the sample receptacle and its associated valve and the opposing plates.

The opposing plates hold the sample receptacle and its associated valve between them by means of at least one threaded rod 34, fitted with a spring 36, which normally biases the plates toward each other, thus holding the sample receptacle with its associated valve securely between the opposing plates. Other mechanical means could be used to bias the plates toward each other.

When preparing to take a sample with the sample station, the valve 12 on the downstream end of the receptacle 10 is opened, then the filling valve 18 is opened. If desired, an automatically controlled valve can be used on the sample receptacle and on the filling valve. Opening the valve allows fluid to flow through the filling pipe, then the sample receptacle and its associated valve, and finally out through the drain line into the overflow/vent pipe. Once it is desired to take a sample, the valve downstream of the receptacle is closed, and the fluid to be sampled will begin to fill the receptacle. When the desired amount of fluid is in the receptacle, the filling valve is closed. During the sampling process, displaced air escapes through the overflow/vent line. If too much fluid flows into the receptacle, the excess flows out through the overflow/vent line and into the drain pipe. If the sample is to be evaluated on appearance, such as color or opacity, the sample can be viewed in place. Otherwise, the sample receptacle can be removed from the sample station. If desired, a second sample receptacle can be put into the sample station for the next sampling event.

The sample receptacle is made of a material that is transparent or translucent. This allows a visual inspection of the sample or of the fluid to be sampled. The person taking the sample can allow the fluid to be sampled to run through the receptacle until such time as it is desired to take a sample. For example, if the fluid tends to separate, the filling valve and the valve attached to the receptacle can both be opened, allowing the fluid to flow through the receptacle until it appears to have the desired characteristics. At this time, the receptacle valve would be closed, allowing the sample to accumulate in the receptacle until the desired amount was obtained, then the filling valve would be closed.

For high temperature applications, or applications where the sample receptacle will be exposed to extremes of pH, the sample receptacle is made of Teflon® or other material that will not degrade in the presence of high temperature fluids.

The sample receptacle is removable from the sample station by rotating a lever 38 or similar device which causes a cam 40 to rotate which forces the two support plates to slide against each other, pushing the opposing plates apart a sufficient distance to allow the removal of the sample receptacle 10 and associated valve. The cam is in a location where its rotation will force the two support plates apart. It has a flattened edge that can press against an abutment 46 on one of the support plates or against an opposing plate when the frame assembly is in the open position, thus locking the frame assembly in place. Once the sample receptacle and associated valve have been removed, a second sample receptacle and valve can be put into the sample station, the lever can be reversed, the spring or springs 36 force the opposing plates together, and the sample station is ready for use.

The sample receptacle and associated valve, once removed, can be set flat on any level surface as the valve acts as a stable base for the sample receptacle, making it less likely to tip over.

Figure 10:
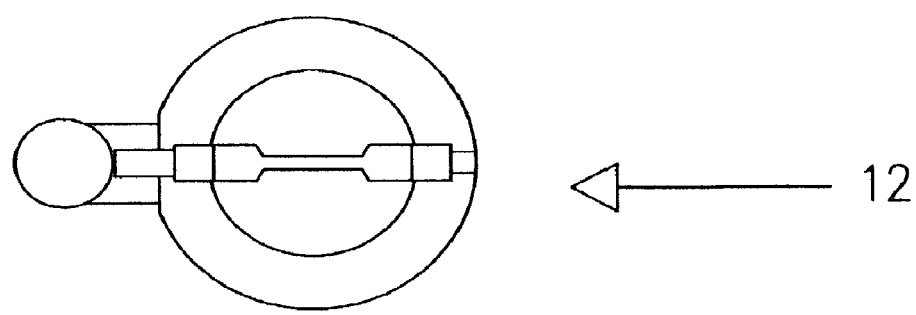
FIG. 10 is a top view of the butterfly valve.
Figure 11:
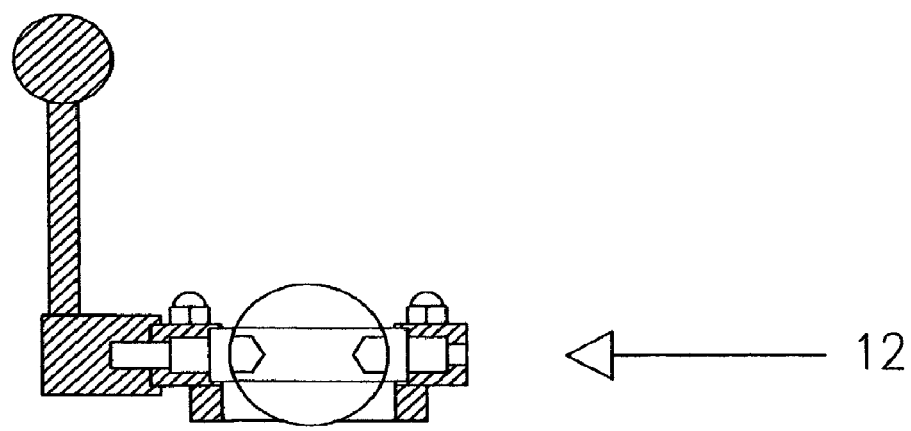
FIG. 11 is a side view of the butterfly valve.

In the case of samples with high viscosity or other characteristics that make it difficult to remove the sample from the receptacle, the valve can be opened to more quickly drain the receptacle. Additionally, the valve makes cleaning of the sample receptacle easier and faster, as water or other cleaning fluid can be run through the receptacle when the valve is open. A butterfly valve can be used as it has a low profile and provides a full open space for drainage. Details of the butterfly valve are shown in FIG. 10 and FIG. 11.

While the sample receptacle can be a variety of shapes, a cylinder allows for easy cleaning. Indicia 80 on the side of the receptacle will allow measurement of the volume or amount of the sample.

The orientation in the claims is for the convenience of the reader and should not be considered limiting.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method for taking a sample comprising:
providing a liquid sample station which may be secured to a discharge line of an apparatus which requires liquid sampling, the sample station including a frame assembly which has two opposing plates and, between them, a removable receptacle having first and second upper and lower ends with a first valve at the lower end of the receptacle, means to vent the receptacle during filling, and a second valve upstream of the receptacle;
opening the first valve;
opening the second valve;
initiating fluid flow through the receptacle until such time as it is desired to take a sample;
closing the first valve;
allowing the fluid which is to be sampled to continue to flow into the receptacle until it reaches the desired amount, and closing the second valve, stopping the flow of fluid into the receptacle.

2. The method of claim 1 in which the receptacle is removed from the frame assembly by rotating a lever which causes a cam to rotate which forces the opposing plates apart, thus allowing the receptacle to be removed from the frame assembly of the liquid sample station after filling.

3. The method of claim 1 in which the receptacle is removed from the frame assembly by rotating a lever which causes a cam to rotate which forces the opposing plates apart, thus allowing the receptacle to be removed from the frame assembly of the liquid sample station after filling, and replaced.

4. A sample station comprising:
a frame assembly;
a tubular receptacle having first and second upper and lower ends, with the first end being open and where the opening in the first upper end of the receptacle is almost as wide as or as wide as the receptacle;
a valve secured to the second lower end where the opening in the valve is almost as wide as the body of the receptacle;
means for releasably holding the receptacle and associated valve in the frame assembly;
means for filling the receptacle; and
means for automatically and continuously venting the receptacle during filling to prevent pressure build-up within the receptacle.

5. The sample station as set forth in claim 4 in which the valve on the second end of the receptacle is an automatically controlled valve.

6. The sample station as set forth in claim 4 in which the means for filling the receptacle is a filling pipe upstream of the receptacle, and which pipe contains a filling valve.

7. The sample station as set forth in claim 6 in which the filling valve is an automatically controlled valve.

8. The sample station as set forth in claim 4 in which the means for filling the receptacle is a filling pipe upstream of the receptacle, and which pipe contains a filling valve, and in which the means for venting the receptacle is a vent pipe upstream of the receptacle and downstream of the filling valve; the upstream end of the vent pipe being flush with or nearly flush with and interior to the downstream end of the filling pipe and in which the vent pipe extends from the location flush with or nearly flush with and interior to the downstream end of the filling pipe, then upstream through the filling pipe for a distance then through an opening which is provided in the wall of the filling pipe, where the vent pipe is attached with a fluid-proof attachment to the circumference of the opening in the wall of the filling pipe and from there, into a drain/overflow pipe.

9. The sample station as set forth in claim 8 in which any overflow from the tubular receptacle flows out through the vent pipe and into the drain pipe.

10. The sample station as set forth in claim 4 in which said frame assembly has two opposing plates, a first plate and a second plate; and in which the first opposing plate is held by a first support plate and the second opposing plate is held by a second support plate; and which support plates are held slidably against each other by means of a channel shaped portion or similar structure on either one of the plates.

11. The sample station as set forth in claim 10 in which each of the opposing plates defines a hole and in which the filling pipe is attached to the circumference of the hole in the first opposing plate, and a drain line is attached to the circumference of the hole in the second opposing plate.

12. The sample station as set forth in claim 10 in which the frame assembly has a lever or other means to rotate a cam which causes the two support plates to slide against one another thus pushing the two opposing plates apart a sufficient distance to allow the removal of the tubular receptacle and valve, and which cam is configured so that it will allow the two opposing plates to be locked into a separated or open position.

13. The sample station as set forth in claim 10 in which the opposing plates on the frame assembly are fitted with at least one threaded rod fitted with a spring or other means which normally biases the plates toward each other, and which serves to hold the tubular receptacle and its attached valve between the two opposing plates.

14. The sample station as set forth in claim 11 in which the two surfaces of the opposing plates that face each other are each provided with a depression or similar indentation around the holes, and wherein a gasket is received in each depression to form a fluid-tight seal between the tubular receptacle or valve and the opposing plates when the frame is in the closed position.

15. The sample station as set forth in claim 6 in which the flow of the fluid through the device is through the filling valve and filling pipe, into the receptacle through the open upper end, through the receptacle and the associated valve secured to the second end of the receptacle, through a drain line and finally into a drain pipe; with any venting or flashing fluids or any overflow during filling flowing through an vent pipe into the drain pipe, thus avoiding pressurizing the receptacle.

16. A tubular receptacle for use with a sample station having a frame assembly; the tubular receptacle having a first and second ends: characterized by the first end being open capable of being sealingly secured to the frame assembly in a leak-free manner and the second end being provided with a valve, and which valve, when closed, functions as a base for the receptacle, providing a surface on which the receptacle and valve can rest.

17. The tubular receptacle and valve as set forth in claim 16 in which the receptacle is made of a material which will not degrade in the presence of high- or low-temperature fluids or extremes of pH.

18. The tubular receptacle and valve as set forth in claim 16 in which the receptacle is made of a material that is transparent or translucent.

* * * * *